(12) United States Patent
Hamada et al.

(10) Patent No.: US 10,302,638 B2
(45) Date of Patent: May 28, 2019

(54) ANALYZING APPARATUS

(71) Applicants: SYSTEM INSTRUMENTS CO., LTD., Tokyo (JP); HIROSAKI UNIVERSITY, Aomori (JP); NATIONAL UNIVERSITY CORPORATION KOBE UNIVERSITY, Hyogo (JP)

(72) Inventors: Kazuyuki Hamada, Tokyo (JP); Takeshi Akiba, Tokyo (JP); Chikara Ohyama, Aomori (JP); Tohru Yoneyama, Aomori (JP); Yuki Tobisawa, Aomori (JP); Toshifumi Takeuchi, Hyogo (JP)

(73) Assignees: SYSTEM INSTRUMENTS CO., LTD., Tokyo (JP); HIROSAKI UNIVERSITY, Aomori (JP); NATIONAL UNIVERSITY CORPORATION KOBE UNIVERSITY, Hyogo (JP)

( * ) Notice: Subject to any disclaimer, the term of this patent is extended or adjusted under 35 U.S.C. 154(b) by 256 days.

(21) Appl. No.: 15/115,234

(22) PCT Filed: May 19, 2014

(86) PCT No.: PCT/JP2014/002630
§ 371 (c)(1),
(2) Date: Jul. 28, 2016

(87) PCT Pub. No.: WO2015/177823
PCT Pub. Date: Nov. 26, 2015

(65) Prior Publication Data
US 2016/0341725 A1    Nov. 24, 2016

(51) Int. Cl.
*G01N 35/00*    (2006.01)
*G01N 35/10*    (2006.01)
(Continued)

(52) U.S. Cl.
CPC ........ *G01N 33/54386* (2013.01); *B01L 9/543* (2013.01); *C12Y 304/21077* (2013.01);
(Continued)

(58) Field of Classification Search
None
See application file for complete search history.

(56) References Cited

U.S. PATENT DOCUMENTS 4,420,254 A    12/1983   Smeaton
6,143,250 A    11/2000   Tajima
(Continued)

FOREIGN PATENT DOCUMENTS

JP    S5526454 A     2/1980
JP    S55157751 U    11/1980
(Continued)

OTHER PUBLICATIONS

Japan Patent Office, Office Action Issued in Application No. 2016-520811, dated Aug. 29, 2017, 8 pages. (Submitted with Machine Translation).

(Continued)

*Primary Examiner* — Kathryn Wright
(74) *Attorney, Agent, or Firm* — McCoy Russell LLP

(57) ABSTRACT

An automatic analyzing apparatus 10 includes a chip rack 11 that stores a pipette chip, a pipette 12 into which a specimen is injected, a conveyance unit that conveys the pipette 12 by parallel translation, a reagent rack 14, a reaction unit 15, a detection unit 16, and a detection block unit 17. The pipette chip stored by the chip rack 11 has a planar structure to directly and optically detect the specimen. The chip rack 11 includes, in a hole that receives the pipette chip, a guide corresponding to the structure of the pipette chip. The pipette 12 sucks or discharges the specimen via the pipette chip mounted onto the tip thereof by a drive of a pump. In
(Continued)

the detection unit 16, a measurement is carried out with the pipette chip arranged so that the plane that receives light is vertical to an optical axis.

13 Claims, 11 Drawing Sheets

(51) Int. Cl.
  *G01N 33/543*  (2006.01)
  *G01N 21/59*  (2006.01)
  *G01N 21/03*  (2006.01)
  *G01N 21/64*  (2006.01)
  *G01N 33/573*  (2006.01)
  *B01L 9/00*  (2006.01)

(52) U.S. Cl.
  CPC ......... *G01N 21/0303* (2013.01); *G01N 21/59* (2013.01); *G01N 21/6428* (2013.01); *G01N 33/573* (2013.01); *G01N 35/00029* (2013.01); *G01N 35/1011* (2013.01); *G01N 2021/6439* (2013.01); *G01N 2035/1062* (2013.01); *G01N 2201/068* (2013.01); *G01N 2333/96455* (2013.01)

(56) References Cited

U.S. PATENT DOCUMENTS

| | | | |
|---|---|---|---|
| 7,727,480 | B2 | 6/2010 | Tajima |
| 2002/0057994 | A1 | 5/2002 | Skeen |
| 2008/0248586 | A1* | 10/2008 | Tajima ................ B01L 3/502 |
| | | | 436/164 |
| 2008/0257073 | A1* | 10/2008 | Tajima ................ B01L 3/0275 |
| | | | 73/864.11 |
| 2014/0273277 | A1* | 9/2014 | Diamond ........... G01N 35/1011 |
| | | | 436/501 |
| 2015/0260720 | A1 | 9/2015 | Ohyama et al. |

FOREIGN PATENT DOCUMENTS

| | | |
|---|---|---|
| JP | S5861447 A | 4/1983 |
| JP | H0213857 A | 1/1990 |
| JP | H04138368 A | 5/1992 |
| JP | H08271336 A | 10/1996 |
| JP | H11502937 A | 3/1999 |
| JP | 2009516188 A | 4/2009 |
| JP | 2011232247 A | 11/2011 |
| WO | 9705492 A1 | 2/1997 |
| WO | 9726539 A1 | 7/1997 |
| WO | 2006062236 A1 | 6/2006 |
| WO | 2007057655 A1 | 5/2007 |
| WO | 2014057983 A1 | 4/2014 |

OTHER PUBLICATIONS

European Patent Office, Partial Supplementary European Search Report Issued in Application No. 14892855.9, dated Dec. 14, 2017, Germany, 9 pages.

ISA Japanese Patent Office, International Search Report Issued in Application No. PCT/JP2014/002630, dated Jul. 29, 2014, WIPO, 5 pages.

* cited by examiner

[図7]

ANALYZING APPARATUS

CROSS REFERENCE TO RELATED APPLICATION

The present application is a U.S. National Phase of International Patent Application Serial No. PCT/JP2014/002630, entitled "ANALYSIS DEVICE," filed on May 19, 2014, the entire contents of which are hereby incorporated by reference for all purposes.

TECHNICAL FIELD

The present invention relates to an analyzing apparatus, and relates to, for example, an automatic analyzing apparatus that detects a specimen such as a prostate specific antigen.

BACKGROUND ART

In conventional automatic analyzing apparatuses, a specimen is sucked from a sample container and is introduced to a well on a plate or a measurement cell, a measurement is performed by fluorescence or spectroscopy, and the concentration of the specimen is detected. In the automatic analyzing apparatuses, it is required to increase the sensitivity of the measurement.

One of the fields in which an analysis with highly-sensitive detection is required is a measurement of the concentration of a prostate specific antigen (PSA) in blood. The measurement of the concentration of the prostate specific antigen in blood is promising with regard to the diagnosis of prostate cancer. Patent Literature 1 discloses one example of the measurement.

In Patent Literature 1, after an 8A6 monoclonal antibody is immobilized on magnetic beads, the magnetic beads are injected into each well on a plate. Then blocking is performed according to a procedure of a sandwich ELISA method, and an HYB4 monoclonal antibody, which is a primary antibody, is added and the obtained solution is mixed into an analyte. After that, a fluorochrome-labeled antibody is added and the resulting solution is left at room temperature. Then the plate is subjected to flow cytometry to detect fluorescence.

CITATION LIST

Patent Literature

[Patent Literature 1] International Patent Publication No. WO 2014-057983
[Patent Literature 2] Japanese Unexamined Patent Application Publication No. H2-13857
[Patent Literature 3] Published Japanese Translation of PCT International Publication for Patent Application, No. 2009-516188

SUMMARY OF INVENTION

Technical Problem

When the fluorescence analysis is carried out by injecting the reagent and the analyte into the plate including the well like in Patent Literature 1, the plate after use thereof is discarded, which increases the amount of waste. Further, when the specimen is moved to the well by a pipette, the amount of specimen that can be used for the measurement is reduced. Further, when the fluorescence emitted by the specimen in the well is measured, the florescence of other specimens that remain in an adjacent well may cause noise. Furthermore, even when the specimen in the adjacent well is removed after the measurement, the specimen cannot be completely cleaned. The specimen that remains in the well may emit afterglow, which may cause noise.

As a method of solving the above problems, Patent Literature 2 and 3 disclose performing the measurement while a specimen is being kept in a pipette or a pipette chip.

However, when the specimen inside the pipette or the pipette chip is measured, since the cross sectional shape of the pipette chip is a circle, an incident light and an output light become a stray light after being refracted by the curved surface of the pipette chip, which causes noise when the measurement is performed. When the prostate specific antigen is detected, in particular, it is desired to perform the measurement with a high sensitivity and with a small amount of a specimen. The noise caused by the stray light inhibits the highly sensitive measurement.

The present invention aims to provide an automatic analyzing apparatus that achieves a highly sensitive measurement by reducing the noise caused by the stray light. The present invention especially aims to provide an automatic analyzing apparatus that detects the prostate specific antigen in which a highly sensitive measurement can be achieved by reducing the noise due to the stray light and other specimens.

Solution to Problem

An automatic analyzing apparatus according to the present invention includes: a pipette chip rack having at least one plane and capable of holding one or a plurality of pipette chips, each of the pipette chips including a measurement cell part through which light can be transmitted; a pipette on which the pipette chip is mounted, the pipette sucking and discharging a specimen; a conveyance means for conveying the pipette on which the pipette chip has been mounted; and a measurement unit including an opening that receives the pipette chip therein and measuring light emitted from the specimen inside the pipette chip, in which: the pipette chip rack includes a guide that orients one plane of the pipette chip in a specific direction on a horizontal surface, the conveyance means conveys, after the pipette chip arranged in the pipette chip rack is mounted on the pipette, the pipette chip into the measurement unit and arranges the pipette chip so that the plane of the pipette chip become orthogonal to an optical axis of the measurement unit, and the measurement unit measures light emitted from the specimen in the pipette chip or light that has transmitted the specimen.

According to the above structure, the incident light and the emitted light rarely become the stray light due to the curved surface when the measurement is performed, whereby noise is reduced and the highly sensitive measurement can be performed.

In the automatic analyzing apparatus according to the present invention, the pipette chip rack includes the guide that orients one plane of the pipette chip in a direction vertical to the optical axis of the measurement unit, and the conveyance means mounts the pipette chip arranged in the pipette chip rack onto the pipette and then conveys the pipette chip into the measurement unit by parallel translation.

According to the above structure, there is no need to provide additional structures and perform additional operations to adjust the direction of the pipette chip with respect to the optical axis. That is, it is possible to achieve a reduction in the number of components of the automatic analyzing apparatus and the number of processes thereof, a reduction in the number of pipette chips that are consumed, and a highly sensitive measurement.

In the automatic analyzing apparatus according to the present invention, the pipette chip rack is tapered above an upper part of the guide.

According to the above structure, it is possible to hold the pipette chip and to orient the plane of the measurement cell part of the pipette chip in a predetermined direction with respect to the horizontal surface.

The automatic analyzing apparatus according to the present invention includes a light shielding means having a nested structure in the opening and the pipette of the detection unit so that the light shielding means corresponds to the opening and the pipette of the detection unit.

According to the above structure, the light shielding can be performed without a contact between the dark box and the light shielding member, whereby it is possible to sufficiently shield light also in a space into which the pipette is inserted from the opening part without requiring highly accurate machine processing.

The automatic analyzing apparatus according to the present invention includes a control means for controlling the conveyance means and the detection unit, in which: the control means moves the pipette in a vertical direction in a position of the opening and outputs an instruction to stop the pipette at a plurality of heights to the conveyance means, and the control means divides the intensity of the signal received by the detection unit for each height at which the pipette is stopped and outputting the signal.

According to the above structure, when the measurement is performed in a plurality of positions corresponding to the reaction plate, noise caused by the stray light and the external light can be reduced and the highly-sensitive light measurement can be performed.

The automatic analyzing apparatus according to the present invention includes a pump unit that sends gas to the pipette, in which the pipette includes a hollow part that communicates the pump unit with the pipette chip and supplies the gas to the pipette chip.

According to the above structure, all of the suction of the specimen or the reagent, the stirring, the cleaning, the reaction, and the detection due to the suction and the discharge can be achieved in the pipette chip.

An analysis system according to the present invention includes the analyzing apparatus stated above and a pipette chip having at least one plane and a measurement cell part through which light can be transmitted, in which: the conveyance means mounts the pipette chip arranged in the pipette chip rack onto the pipette, conveys the pipette chip into the measurement unit, and arranges the pipette chip so that the plane of the pipette chip becomes orthogonal to the optical axis of the measurement unit, and the measurement unit measures light emitted by the specimen in the pipette chip.

According to the above structure, the incident light and the emitted light rarely become the stray light due to the curved surface when the measurement is performed, whereby noise is reduced and the highly sensitive measurement can be performed.

In the analysis system according to the present invention, the analyzing apparatus includes a reagent rack including one or a plurality of wells, each containing a reagent, the pipette chip includes a reaction plate in the chip, and the pipette sucks the reagent included in the well into the pipette chip and causes the reaction plate and the reagent to be reacted.

In the analysis system according to the present invention, the analyzing apparatus includes a reagent rack including one or a plurality of wells, each containing the reagent, the pipette chip includes a reaction plate in the chip, the reaction plate having a front surface including the reagent, and the pipette sucks the reagent included in the well into the pipette chip and causes the reagent included in the reaction plate and the reagent that has been sucked to be reacted.

According to the above structure, all of the suction of the specimen or the reagent, the stirring, the cleaning, the reaction, and the detection due to the suction and the discharge can be achieved in the pipette chip.

In the analysis system according to the present invention, the reagent rack holds, in each well, an antibody and a fluorescent label that specifically react against a prostate specific antigen in which a terminal sialic group is linked to galactose at a position of $\alpha 2,3$, the reaction plate immobilizes an antibody that specifically reacts against a free prostate specific antigen, by a sandwich ELISA method, the antibody and the florescent label react against the prostate specific antigen in the specimen to form a complex, and the measurement unit measures fluorescence emitted by the complex.

According to the above structure, the prostate specific antigen can be detected with a high sensitivity.

In the analysis system according to the present invention, the reaction plate includes a plurality of sections on which different reagents are immobilized.

According to the above structure, the present invention can deal with a plurality of analytic items.

In the analysis system according to the present invention, one of the sections does not immobilize the reagent.

According to the above structure, the present invention can be applied to measure a blank. Further, according to the above structure, a modification may be performed later.

An analysis system according to the present invention is an operation method of the automatic analyzing apparatus described above, the operation method including the processes of: moving, by the conveyance means, the pipette to a position directly above the pipette chip placed on the pipette chip rack; moving vertically, by the conveyance means, the pipette to mount the pipette chip onto the pipette; sucking, by the pipette, the specimen into the pipette chip; conveying, by the conveyance means, the pipette chip into the detection unit to arrange the pipette chip so that the plane of the pipette chip becomes orthogonal to the optical axis of the measurement unit; and measuring, by the detection unit, light emitted from the specimen in the pipette chip.

According to the above structure, the incident light and the emitted light rarely become the stray light due to the curved surface when the measurement is performed, whereby noise is reduced and the highly sensitive measurement can be performed.

Advantageous Effects of Invention

According to the automatic analyzing apparatus of the present invention, the measurement can be performed at an angle in which the pipette chip having a plane surface on which light impinges is vertical to the optical axis of the measurement, whereby it is possible to reduce the amount of consumption of the pipette chip and to achieve a highly sensitive measurement.

DESCRIPTION OF EMBODIMENTS

First Embodiment

Hereinafter, with reference to the drawings, embodiments of the present invention will be described.

Figure 1:
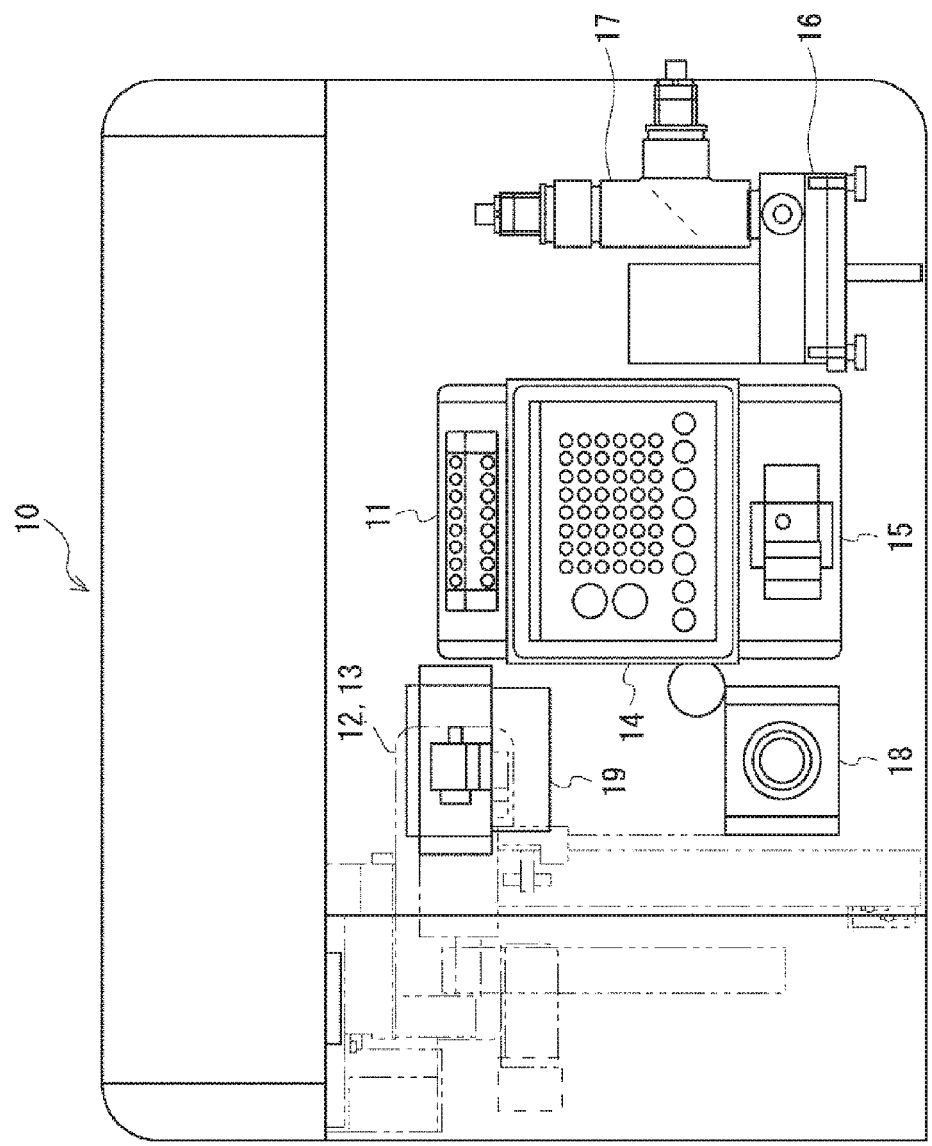
FIG. 1 is a plan view of an automatic analyzing apparatus according to a first embodiment.

FIG. 1 is a plan view of an automatic analyzing apparatus according to a first embodiment. FIG. 1 is a top view showing a state in which the automatic analyzing apparatus is placed on a test board or the like in a normal usage state. That is, the direction that is vertical to the paper of FIG. 1 corresponds to the vertical direction in the automatic analyzing apparatus usage state.

Figure 2:
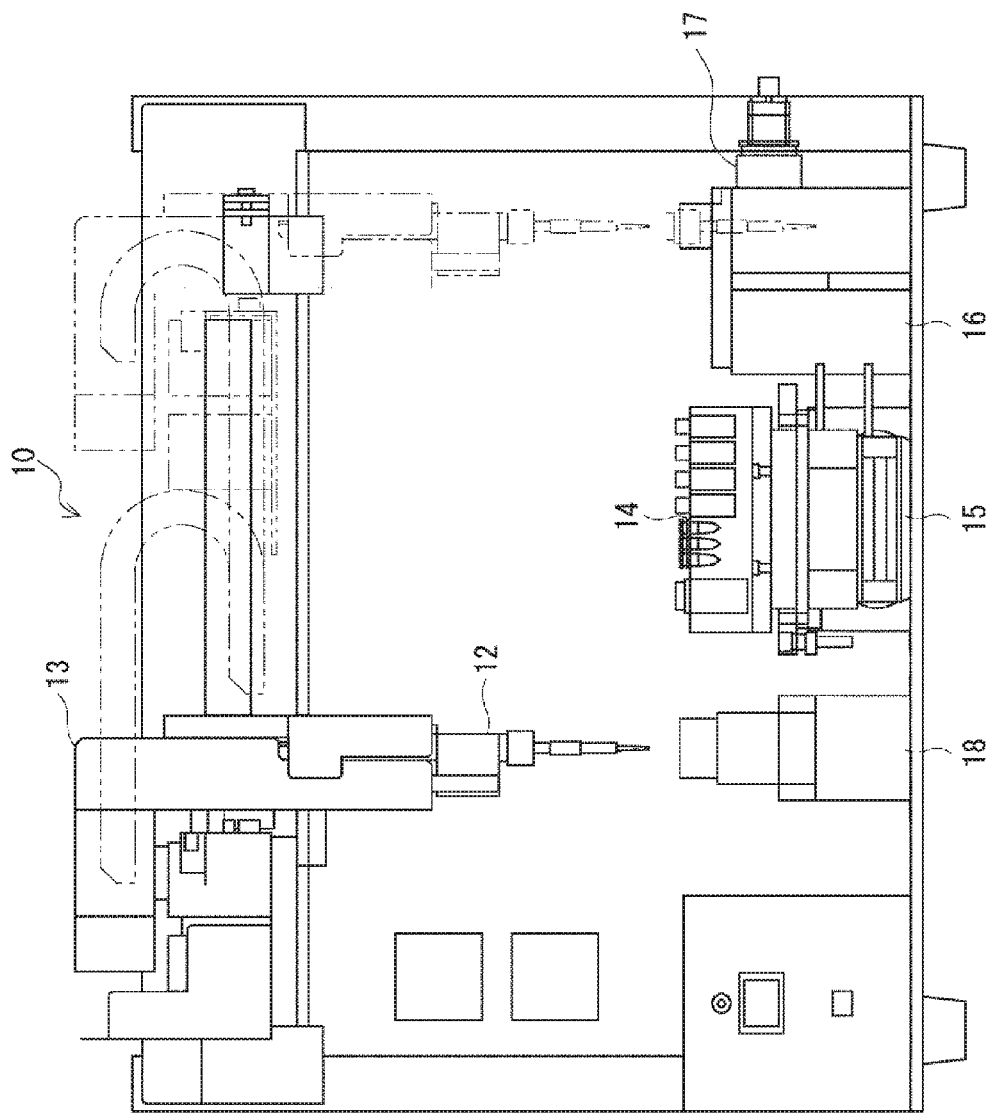
FIG. 2 is a front view of the automatic analyzing apparatus according to the first embodiment.

FIG. 2 is a front view of the automatic analyzing apparatus according to the first embodiment. FIG. 2 is a front view showing a state in which the automatic analyzing apparatus is placed on the test board or the like in the normal usage state. That is, the vertical direction in the paper of FIG. 2 corresponds to the vertical direction in the automatic analyzing apparatus usage state.

The automatic analyzing apparatus 10 includes a chip rack 11 that stores pipette chips, a pipette 12 into which a specimen is injected, a conveyance unit 13 that conveys the pipette 12 by parallel translation, a reagent rack 14, a reaction unit 15, a detection unit 16, a detection block unit 17, a waste bottle 18, and a chip disposal box 19.

Each of the pipette chips stored in the chip rack 11 has a planar structure to directly and optically detect the specimen. Therefore, the chip rack 11 includes guides corresponding to the structure of the pipette chips in holes that accommodate the respective pipette chips. The chip rack 11 includes one or a plurality of holes that include the respective guides. When the chip rack 11 includes the plurality of holes, the holes may be linearly arranged and the guides of the respective holes may be linked together, and the start position of the conveyance unit 13 is preferably arranged in an extension of the line where the holes are arranged. Further, the holes may be arranged in a plurality of lines. The structure of the pipette chips received by the holes and the details of the chip rack 11 will be described later.

The pipette 12 has a hollow and tapered structure. The pipette 12 has a tip on which the pipette chip is mounted and the other end including an inner tube connected to an internal pump or an external pump unit, and the hollow part in the tip and the internal pump or the inner tube are communicated with each other. The pipette 12 sucks or discharges the specimen via the pipette chip mounted on the tip by a drive of a pump.

The conveyance unit 13 includes a conveyance mechanism that holds the pipette 12 and translates the pipette 12 in three axes (front-back direction, lateral direction, and vertical direction). The conveyance unit 13 includes a control unit that controls, for example, a drive means such as a stepping motor or a pulse motor, a transfer means such as a pulley or a belt, a holding means for holding the pipette 12, and a drive means. Further, the conveyance unit 13 can be achieved by a mechanism that drives and controls a robot arm that can hold the pipette 12.

The reagent rack 14 includes a plurality of wells. The sample and the reagent are input to each of the wells.

The reaction unit 15 includes a hole that receives the pipette chip mounted on the pipette 12 and a temperature adjustment mechanism that adjusts the temperature of an analyte and the specimen to the temperature required for a reaction, and promotes the reaction while keeping the temperature of the analyte and the specimen at a constant reaction temperature. The temperature adjustment mechanism includes, for example, a heater or a Peltier element, a temperature sensor, and a control unit that controls the heater so that the pipette chip has a predetermined temperature according to the temperature detected by the temperature sensor.

The detection unit 16 has a structure in which it accommodates the pipette 12 therein and it provides an environment without noise caused by an external light. That is, the detection unit 16 includes a dark box and an opening that receives the pipette chip mounted on the pipette 12 in the dark box.

The detection block unit 17 has a configuration to detect light emitted from the specimen in the pipette chip. Specifically, the detection block unit 17 emits light having a predetermined wavelength onto the specimen in the pipette chip and detects fluorescence emitted from the specimen.

The waste bottle 18 is a bottle that receives the specimen after the measurement and an unreacted reagent. The chip disposal box 19 is a box that contains the pipette chip which is removed from the pipette 12 after the measurement.

Next, a relation of the orientations of the chip rack 11 and the detection unit 16, which is one of the characteristics of the automatic analyzing apparatus 10 according to the first embodiment, will be described. The automatic analyzing apparatus 10 is used for a pipette chip having a plane surface that receives light emitted from a light emission part and the pipette chip has a structure in which the direction of the pipette chip on the horizontal surface in the chip rack 11 arranged in the first stage and the direction thereof on the horizontal surface arranged in the last stage when the measurement is performed become parallel to each other. In the following description, the structure of the chip rack 11 will be described in detail.

The chip rack 11 includes a guide having a planar shape to accommodate the pipette chip having a planar shape. More specifically, the guide of which a part of or the whole inner peripheral surface abuts a plane outer surface of the pipette chip via some clearance is provided in the chip rack 11.

Accordingly, the guide of the chip rack 11 serves as a guide that regulates a rotation around the vertical axis of the pipette chip that is placed on the chip rack 11. That is, the pipette chip is arranged in the guide of the chip rack 11 in a state in which the planar shape of the chip rack 11 faces the planar shape of the pipette chip, whereby the pipette chip is arranged in such a way that the direction thereof on the horizontal surface in the chip rack 11 is oriented in a specific direction.

On the other hand, in the detection unit 16, the pipette chip performs the measurement by arranging the plane that receives light so that it becomes vertical to an optical axis.

In the automatic analyzing apparatus 10 according to the first embodiment, the chip rack 11 is arranged in such a way that the plane of the chip rack 11 becomes vertical to the optical axis described above. That is, the direction of the plane of the pipette chip in the state in which it is accommodated in the chip rack 11 and the direction of the plane of the pipette chip in the state in which it is accommodated in the detection block unit for the measurement become parallel to each other in the direction on the horizontal surface.

As a result, the conveyance unit 13 needs not include the mechanism that rotates the pipette 12 and the pipette chip and is able to make the plane of the pipette chip that receives light vertical to the optical axis only by the conveyance mechanism that translates the pipette 12 in the three axes. Further, the conveyance unit 13 and the detection unit 16 need not include a mechanism to adjust the direction of the pipette chip so that the plane of the pipette chip becomes vertical to the optical axis.

By employing the above arrangement relations, there is no need to provide additional structures and perform additional operations to adjust the direction of the pipette chip with respect to the optical axis. That is, it is possible to achieve a reduction in the number of components of the automatic analyzing apparatus and the number of processes thereof, a reduction in the number of pipette chips that are consumed, and a highly sensitive measurement.

The guide may not have a plane shape as long as it has a function of orienting the planar shape of the pipette chip in a specific direction. The guide may include, for example, a holding part formed of three or more support points corresponding to the plane of the pipette chip and a holding member formed of one or more support points that hold the pipette chip from the rear surface side of the plane. Further, some of the support points may be replaced by a linear or curved holding member.

Further, the optical axis in the above description corresponds to, when light is refracted using a half mirror, an optical axis between the half mirror and the pipette chip. A detection mechanism using the half mirror will be described with reference to FIG. 3.

Figure 3:
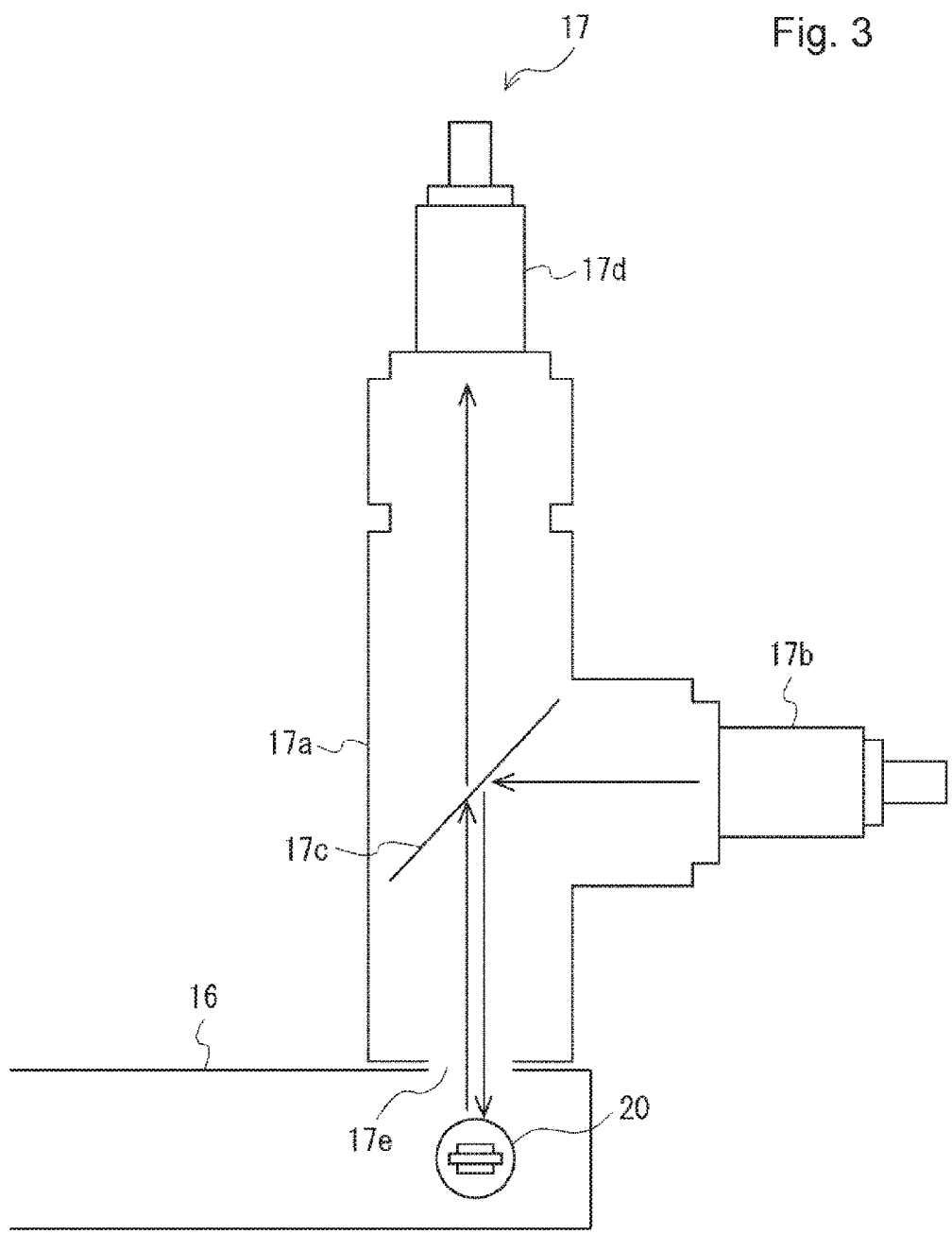
FIG. 3 is a diagram showing details of a detection block unit according to the first embodiment.

FIG. 3 is a diagram showing details of the detection block unit according to the first embodiment.

In FIG. 3, a detection block unit 17 includes a light emission part 17b, a half mirror 17c, and a detector 17d in a dark box 17a. The detection block unit 17 integrates the detection unit 16 and a dark room. The dark boxes are connected together, with a through hole 17e being provided in an optical path of the dark boxes. That is, light emitted from the light emission part 17b impinges on the pipette chip received by the detection unit 16 via the half mirror 17c and the through hole 17e. Then the fluorescence emitted from the pipette chip reaches the detector 17d via the through hole 17e and the half mirror 17c.

As described above, when the light is refracted using the half mirror and refracted light is measured by the detector, the plane of the pipette chip is made vertical to the optical axis between the pipette chip and the half mirror.

Further, the pipette may include a rotation means such as a stepping motor or a pulse motor to rotate the direction of the pipette chip on the horizontal surface. In this case, regardless of the direction in which the chip rack 11 orients the pipette chip in the direction on the horizontal surface, the measurement can be performed. Such a control may be performed to cause the control means to store the angle of the direction of the horizontal surface in which the pipette chip is oriented in the chip rack 11 and the optical axis in advance and the rotation means to rotate the pipette chip so that the plane of the pipette chip reaches the angle perpendicular to the optical axis.

Figure 4:
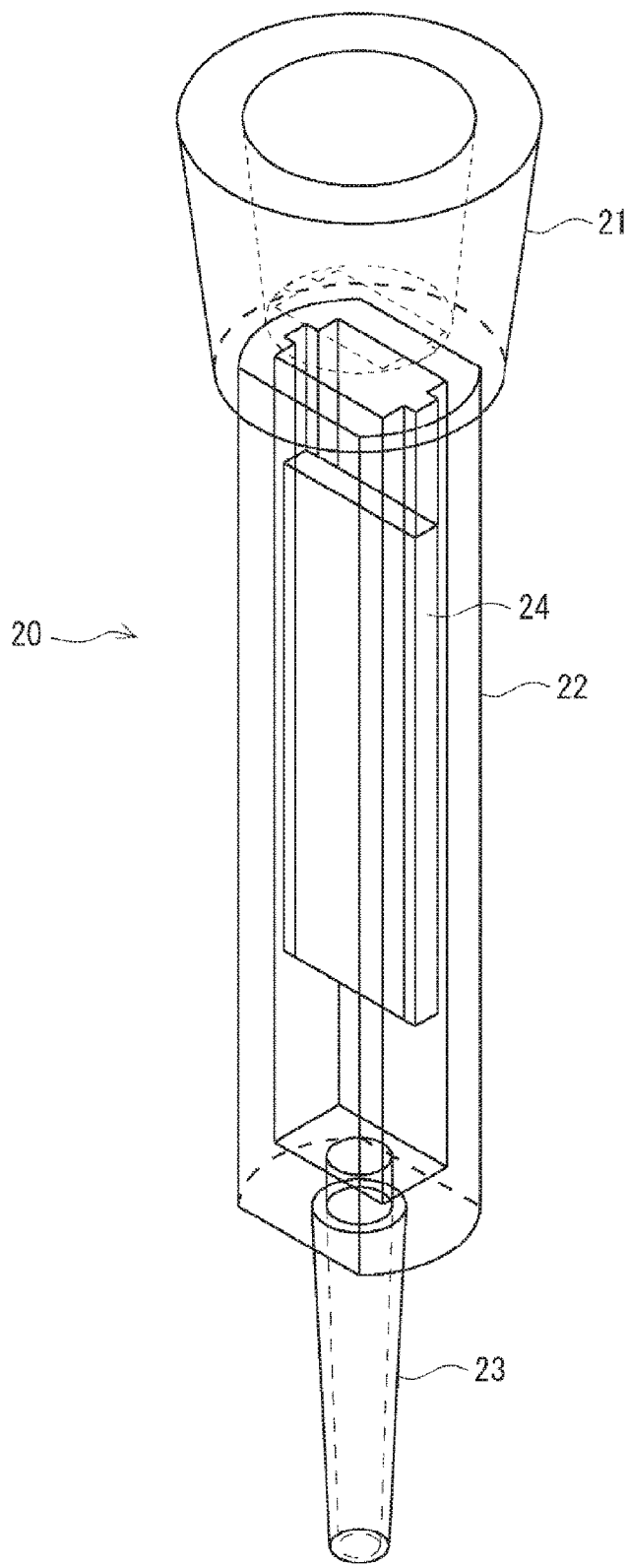
FIG. 4 is a perspective view of a pipette chip according to the first embodiment.
Figure 5:
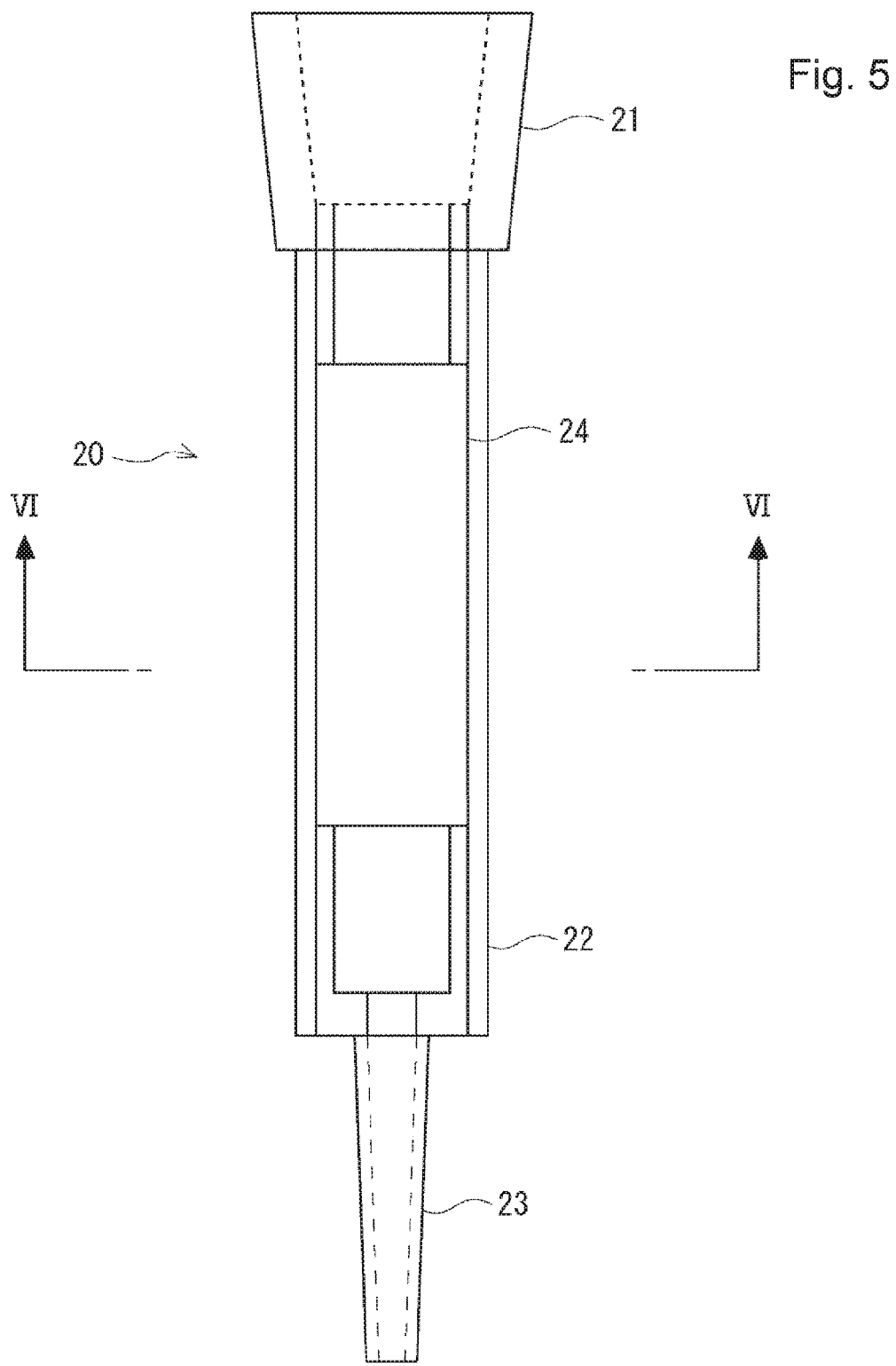
FIG. 5 is a front view of the pipette chip according to the first embodiment.
Figures 6, 7:
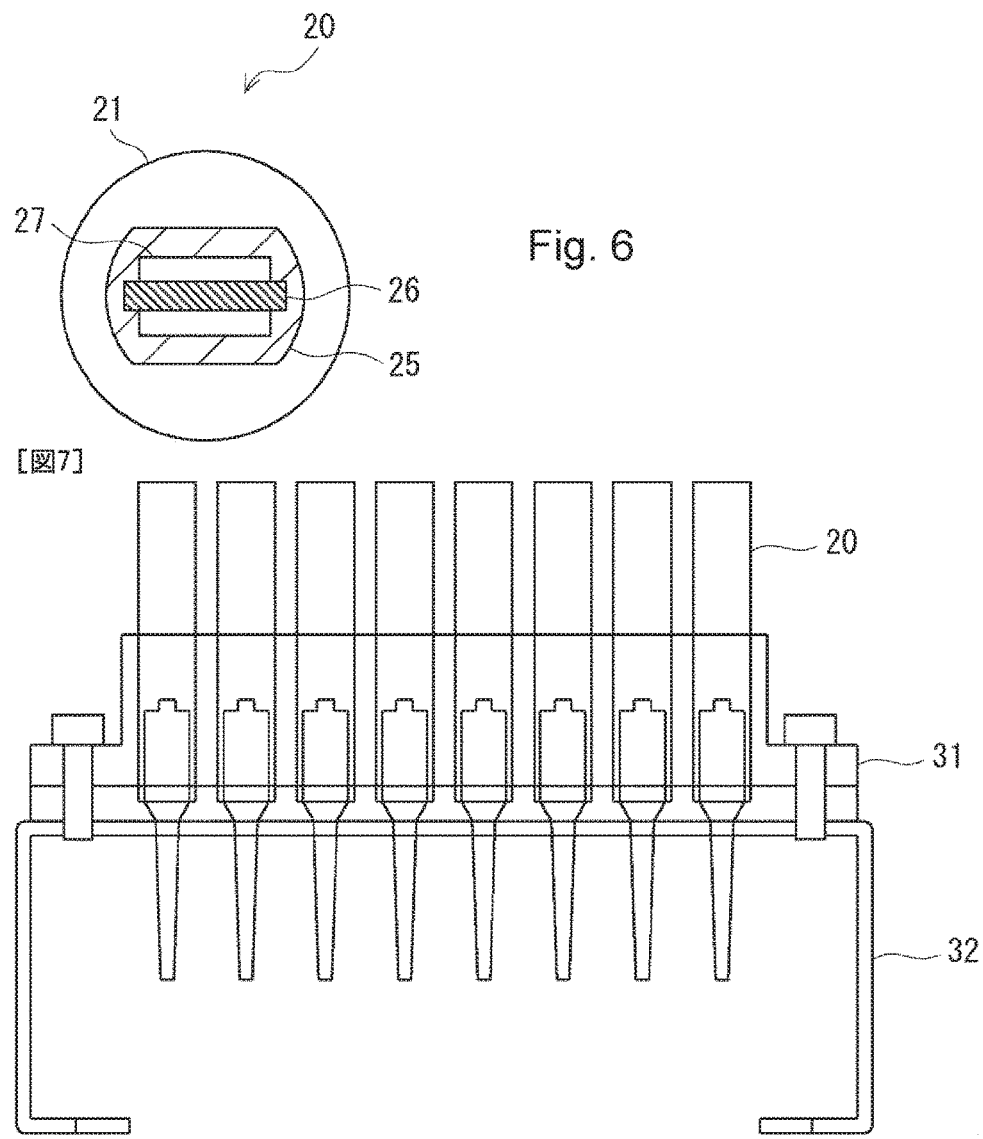
FIG. 6 is a cross-sectional view of the pipette chip according to the first embodiment.
FIG. 7 is a front view of a pipette chip rack according to the first embodiment.

Next, the structure on the side of the pipette chip will be described. FIGS. 4 to 6 are diagrams of the pipette chip according to the first embodiment. FIG. 4 is a perspective view, FIG. 5 is a front view, and FIG. 6 is a cross-sectional view taken along the line VI-VI of FIG. 5.

The pipette chip 20 includes an all-in-one structure in which all of the suction of the specimen or the reagent, the stirring, the cleaning, the reaction, and the detection due to the suction and the discharge are performed in the pipette chip 20. Further, the pipette chip 20 is formed of transparent resin in order to suppress attenuation of the light before the light reaches the inside of the pipette chip 20.

That is, the pipette chip 20 includes an opening part 21 having a cylindrical shape corresponding to the tip of the pipette 12 in the upper end thereof, a rectangular parallelepiped or cylindrical measurement cell part 22 having one or a plurality of planes on the outer surface and the inner surface in the central part thereof, and a tapered nozzle part 23 having a cylindrical shape to suck or discharge the specimen and the reagent in the lower end thereof. The internal spaces of the opening part 21, the measurement cell part 22, and the nozzle part 23 communicate with one another.

Further, a pair of grooves 26 are included in the measurement cell part 22 to arrange and fix the rectangular parallelepiped reaction plate 24 inside thereof. The plane 25 of the measurement cell part 22 and the pair of grooves 26 are formed so that they become parallel to each other and the respective distances between each of the grooves 26 and the plane 25 become equal to each other. That is, in a state in which the reaction plate 24 is fixed using the grooves 26 as a guide, a plane 27 of the reaction plate 24 and a plane 25 of the measurement cell part 22 become parallel to each other. As a result, since the light that is vertically incident on the plane 25 of the measurement cell part 22 is vertically incident on the plane 27 of the reaction plate 24, the angle between the light and the reaction plate 24 becomes optimal for the measurement. The plane 25 of the measurement cell part 22 is preferably a flat surface without irregularities to prevent the light for the measurement from being diffused.

The front surface of the reaction plate 24 may be modified by a reagent such as an antibody or may not be modified. The reaction plate whose front surface has not yet been modified may be modified later by sucking the reagent into the measurement cell part 20 of the pipette chip 20.

Next, a structure of the chip rack corresponding to the pipette chip will be described.

Figure 8:
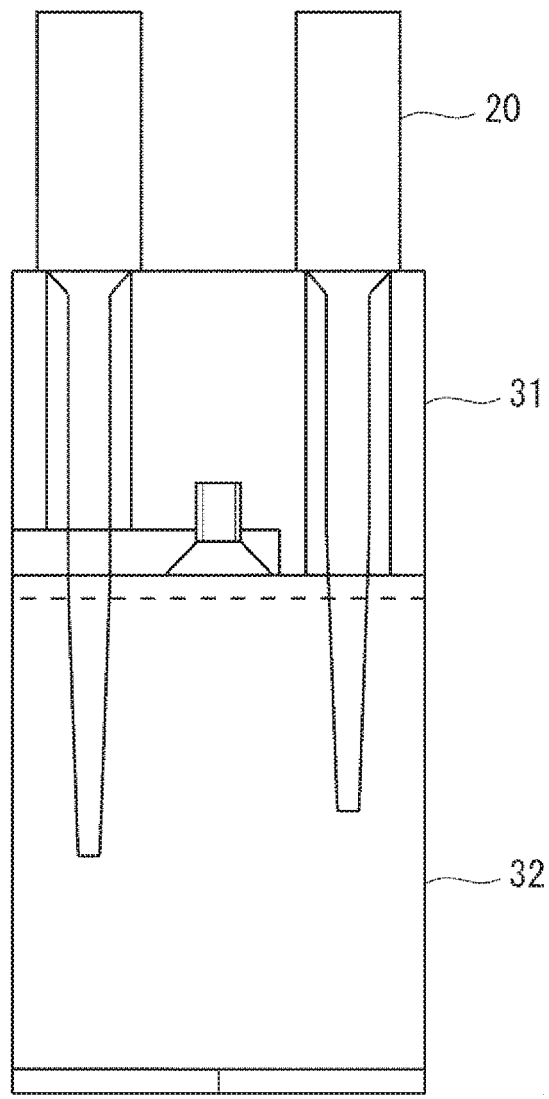
FIG. 8 is a plan view of the pipette chip rack according to the first embodiment.
Figure 9:
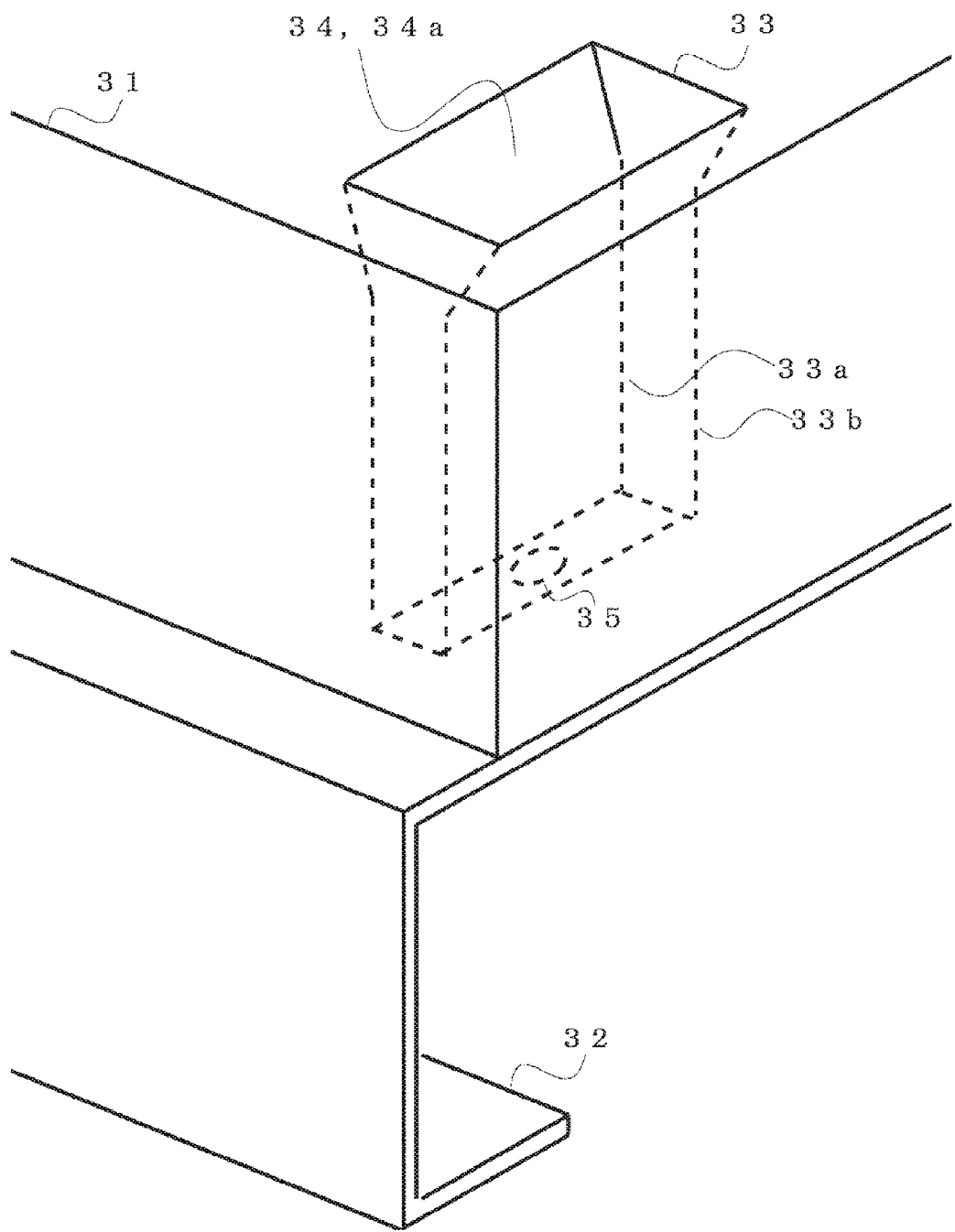
FIG. 9 is a perspective view of the pipette chip rack according to the first embodiment.

FIGS. 7 to 9 are diagrams of the pipette chip rack according to the first embodiment. FIG. 7 shows a front view, FIG. 8 shows a left-side view, and FIG. 9 shows a perspective view. As shown in FIG. 7, the chip rack 11 includes an upper structure 31 and a lower structure 32.

The upper structure 31 includes one or a plurality of holes 33 that receive the pipette chip 20. The hole 33 has a shape corresponding to the plane of the measurement cell part 22 of the pipette chip 20 on the inner surface thereof, that is, a planar structure. When the pipette chip 20 includes two parallel planes, for example, the hole 33 includes two planes 33a and 33b that are parallel to each other, and the distance between the two planes is made equal to the sum of the thickness between the planes of the pipette chip 20 and the gap along which the pipette chip 20 can be slid.

Further, the hole 33 includes a tapered part 34 in the upper part thereof and the upper part of the hole 33 is large in area. Regardless of the direction in which the pipette chip 20 is inserted, the direction of the pipette chip 20 is oriented in one direction as it passes from a slope 34a of the tapered part 34 toward the plane 33a due to the force applied when the pipette chip 20 is inserted and it is moved downward by gravity.

That is, when the direction of the plane 25 of the pipette chip 20 is different from the direction of the plane 33a of the upper structure 31, the downward force due to the gravity or the like acts on the slope 34a of the tapered part 34. While the downward force acts on the slope 34a as components of the force by which the pipette chip 20 goes down the slope and the force that is vertical to the slope of the tapered part, the latter one is in balance with the repulsion force of the slope and only the former one acts on the pipette chip 20.

As a result, in the pipette chip 20, the plane 25 of the measurement cell part 22 is arranged in the same direction as the direction of the plane 33a of the upper structure 31 on the horizontal surface along the plane 33a of the upper structure 31.

The lower structure 32 includes a hole 35 corresponding to the hole 33 when the upper structure 31 is superposed on the lower structure 32. The hole 35 has a shape that is equal to or larger than the cross section of the nozzle part 23 of the pipette chip 20 and is smaller than the cross section of the measurement cell part 22 of the pipette chip 20. That is, the lower structure 32 has a function as a stopper that stops the drop of the pipette chip 20 inserted from the hole 33 of the upper structure 31 at a boundary between the measurement cell part 22 and the nozzle part 23.

According to the above structures, the chip rack 11 is able to hold the pipette chip 20 and to orient the plane of the measurement cell part 22 of the pipette chip 20 in a specific direction on the horizontal surface.

While the hole of the chip rack and the outer surface of the pipette chip need to have one surface that is formed to be a plane, the other surfaces may be formed in various shapes. They may have, besides the plane, a curved surface, for example, so that they have a semi-cylindrical shape, or a polygonal column, or a columnar shape in which the plane and the curve are combined. Further, the shape of the inner surface of the pipette chip is not limited to the one described above, as long as the part that faces the plane has a plane and is parallel to the plane of the outer surface, and may be a polyhedron, a curve, or a composite of the plane and the curve.

Next, an example of measuring a specific antigen in association with the prostate cancer using the automatic analyzing apparatus 10 will be described.

The respective wells of the reagent rack 14 contain a sample (serum), a block solution, an antibody reagent, and a fluorescent reagent. On the other hand, an antibody is immobilized on the front surface of the reaction plate 24 in the pipette chip 20. When the automatic analyzing apparatus 10 is used for a diagnosis of prostate cancer, an anti-free PSA specific monoclonal antibody is immobilized. The anti-free PSA specific monoclonal antibody is an anti-free PSA antibody that does not react with a complex PSA which is derived from clone 2E2. Specific antibodies include an 8A6 monoclonal antibody manufactured by Funakoshi Co., Ltd.

First, the pipette 12 is moved to a position directly above the chip rack 11 and is then moved downward, whereby the pipette chip 20 is mounted on the tip of the pipette 12.

Next, after the pipette 12 is elevated, it moves to a position directly above the reagent rack 14. The pipette 12 is then lowered to a height of the pipette chip 20 in the well of the reagent rack 14, and performs suction, reaction, discharge, and cleaning by a drive of the pump. The operations of the suction, the reaction, the discharge, and the cleaning are respectively executed in the sample (serum), the block solution, the antibody reagent, and the fluorescent reagent.

First, the pipette 12 sucks the blocking solution. Due to the blocking solution, the front surface of the reaction plate 24 is blocked.

Next, the pipette 12 discharges the blocking solution and sucks the sample. The measurement cell part 22 of the pipette chip 20 is filled with the sample. After that, by leaving it at 4° C. for five minutes to one hour, the antibody immobilized on the reaction plate 24 and the free PSA included in the sample are reacted.

Next, the pipette 12 discharges the sample and sucks the antibody reagent. When the automatic analyzing apparatus 10 is used for a diagnosis of prostate cancer, an anti-$\alpha$2,3 linked sugar chain antibody, that is, a monoclonal antibody that specifically recognizes the sugar chain in which terminal sialic acid residues are linked to galactose through an $\alpha$(2,3) linkage, is suitably used. Specific antibodies include an HYB4 monoclonal antibody manufactured by Wako Pure Chemical Industries, Ltd. By leaving it at 4° C. for five minutes to one hour, a complex of anti-free PSA antibody—free PSA—anti $\alpha$2,3 linked sugar chain antibody is formed on the reaction plate 24.

Next, the pipette 12 discharges the antibody reagent and sucks the fluorescent reagent. Specific fluorescent reagents include a fluorescent dye-labeled anti-mouse IgG3 antibody. By keeping it at room temperature for 5 to 45 minutes, a complex of anti-free PSA antibody—free PSA—anti-$\alpha$2,3 linked sugar chain antibody-fluorescent reagent is formed on the reaction plate 24.

After the complex is formed, the pipette 12 moves the pipette chip 20 to the position of the detection unit 16 and lowers the pipette chip 20 at the position of the opening 40a. The detection block unit 17 then detects the fluorescence emitted from the measurement cell part 22 of the pipette chip 20.

After the fluorescence is detected, the pipette 12 moves to a position directly above the waste bottle 18 by elevation and parallel translation, discharges the fluorescent reagent, and discards the fluorescent reagent into the waste bottle 18.

Last, the pipette 12 is moved to the chip disposal box 19, releases the pipette chip 20 by a releasing mechanism of the chip disposal box 19, and discards the pipette chip 20 into the chip disposal box 19.

According to the above operation, the automatic analyzing apparatus 10 is able to detect the prostate specific antigen with a high sensitivity.

While it is required to detect the prostate specific antigen in the order of 10 to 100 pg/mL in the field of the diagnosis of prostate cancer, the automatic analyzing apparatus that corresponds to the pipette chip having the plane that receives light is provided in the first embodiment. Therefore, compared to a case in which the measurement is performed in a state in which the sample is introduced into a typical pipette chip having a circular cross section, the incident light and the emitted light rarely become the stray light due to the curved surface when the fluorescence or the like is measured, whereby the noise can be reduced and the highly sensitive measurement can be performed.

In order to achieve the highly sensitive measurement, it is important to reduce not only the stray light but also noise due to an external light. In particular, the opening part of the dark box into which the pipette chip is inserted needs to have a structure to shield light.

Next, light shielding in the opening part to receive the pipette chip provided in the detection unit 16 of the automatic analyzing apparatus according to the first embodiment will be described.

Figure 10:
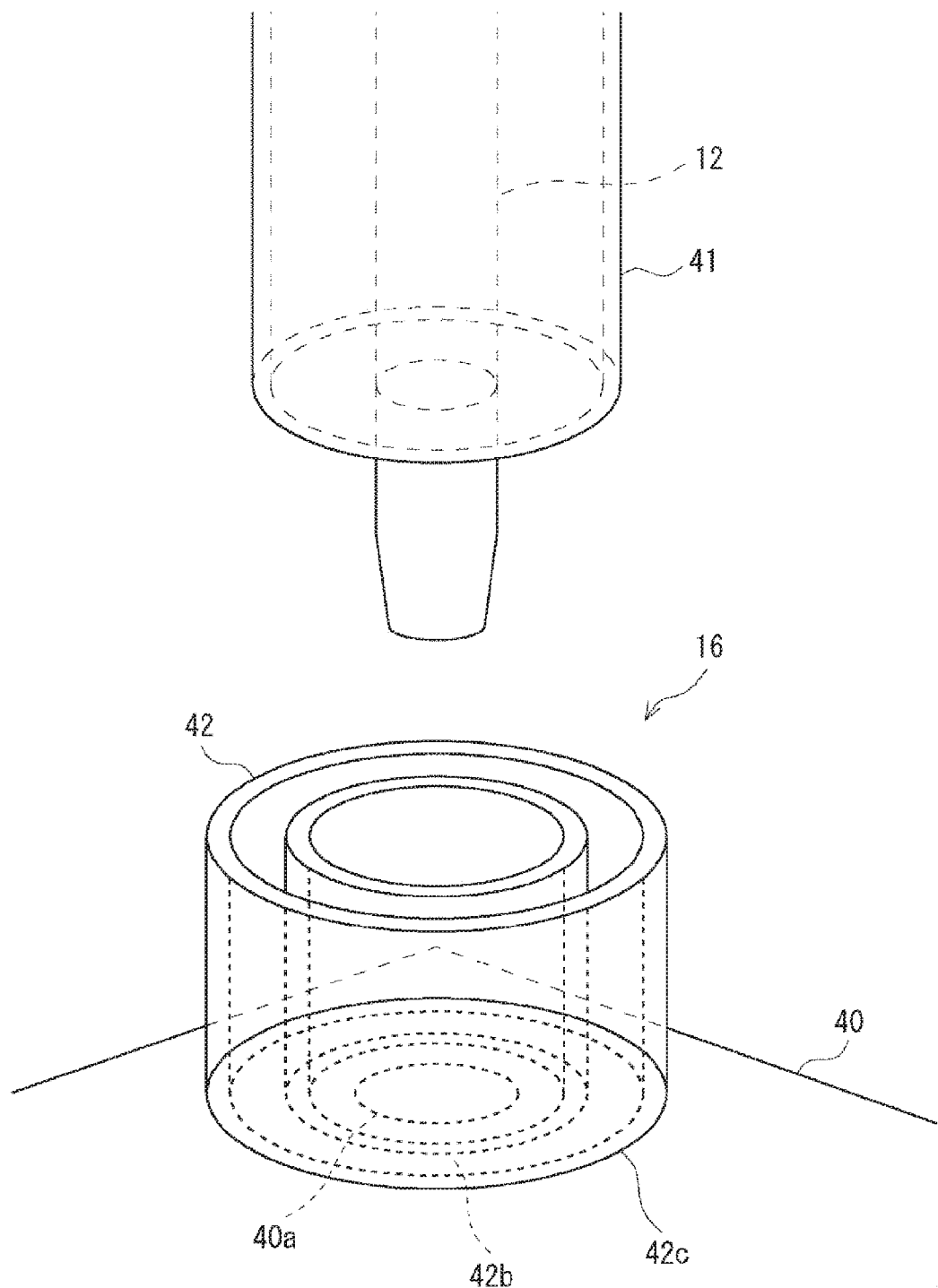
FIG. 10 is a diagram showing a configuration regarding light shielding of the automatic analyzing apparatus according to the first embodiment.

FIG. 10 is a diagram showing a configuration regarding the light shielding of the automatic analyzing apparatus according to the first embodiment. Specifically, FIG. 10 is a diagram for describing the combination of the detection unit 16 and the pipette 12 in a state in which the pipette chip is contained in the detection unit 16.

As shown in FIG. 10, the detection unit 16 includes a dark box 40, an opening 40a that receives the pipette chip mounted on the pipette 12 in the dark box 40, and a dark box-side light shielding part 42 having a cylindrical shape in a position directly above the opening 40a.

The pipette 12 includes a pipette-side light shielding part 41 having a cylindrical shape, one end of the pipette-side light shielding part 41 being closed with a cap, the pipette-side light shielding part 41 of the pipette 12 and the light shielding part 42 of the detection unit 16 are cylinders having diameters different from each other, and the cylinders are nested within each other when the opening 40a of the detection unit 16 accommodates the pipette chip. While the pipette chip that is mounted onto the tip of the pipette 12 is not shown in FIG. 10 in order to clarify the configuration of shielding light by the nested structure, the pipette chip is mounted onto the tip of the pipette 12 in the actual measurement.

That is, the detection unit 16 and the pipette 12 are integrated with each other and light cannot enter from outside. Further, the front surfaces of the dark box 40, the pipette-side light shielding part 41, and the light shielding part 42 are colored black, for example, so that they absorb light, which causes noise.

The pipette 12 includes the pipette-side light shielding part 41 and the detection unit 16 includes the dark box-side light shielding part 42. The detection unit 16 is formed of the dark box 40 and includes the opening 40a to accommodate the pipette chip 20. Therefore, the inner diameter of the opening 40a is larger than the outer diameter of a part around the tip of the pipette chip 20, with some clearance therebetween. The dark box-side light shielding part 42 is provided in a position corresponding to the opening 40a.

The dark box-side light shielding part 42 includes an opening the same as the opening 40a, and a cylindrical inside diameter part 42b and a cylindrical outside diameter part 42c having diameters different from each other. The pipette-side light shielding part 41 has a cylindrical shape having one end that is closed.

Figure 11:
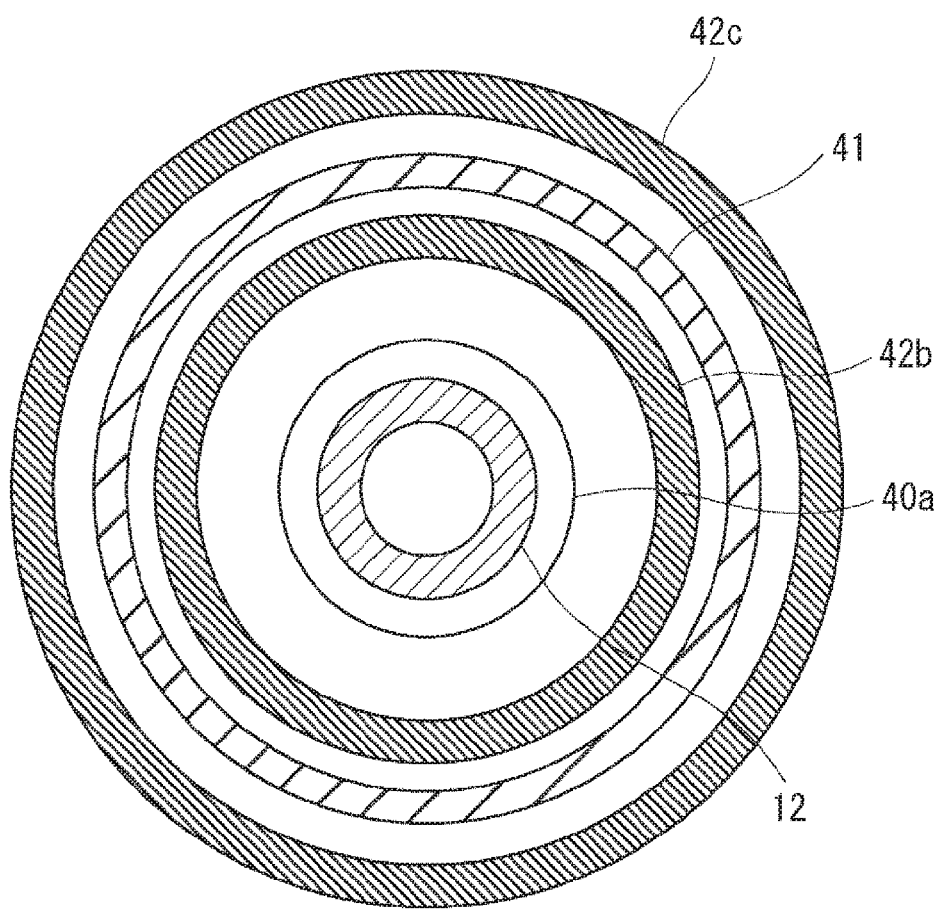
FIG. 11 is a schematic view of a cross section showing a nested structure of a pipette-side light shielding part and a dark box-side light shielding part of the automatic analyzing apparatus according to the first embodiment.

The pipette-side light shielding part 41 and the dark box-side light shielding part 42 have a structure in which the cylindrical parts are nested within each other. FIG. 11 is a schematic view of the cross section indicating the nested structure of the pipette-side light shielding part and the dark box-side light shielding part. That is, FIG. 11 shows a cross section of the pipette-side light shielding part 41 and the dark box-side light shielding part 42 in a state in which the pipette 12 and the detection unit 16 are integrated with each other and the pipette-side light shielding part 41 and the dark box-side light shielding part 42 overlap each other and are nested within each other.

The diameters of the opening 40a, the inside diameter part 42b, the pipette-side light shielding part 41, and the outside diameter part 42c increase in this order. More specifically, the inner diameter of the inside diameter part 42b is larger than the outer diameter of the pipette 12 so that the pipette 12 can be put into the inside diameter part 42b. The inner diameter of the pipette-side light shielding part 41 is larger than the outer diameter of the inside diameter part 42b and is smaller than the inner diameter of the outside diameter part 42c so that the pipette-side light shielding part 41 can be provided between the outer peripheral surface of the inside diameter part 42b and the inner peripheral surface of the outside diameter part 42c.

Further, the pipette-side light shielding part 41, the opening 40a, the inside diameter part 42b, and the outside diameter part 42c are arranged in a concentric circle with the same center. That is, when the pipette 12 is lowered and causes the pipette chip 20 to be inserted into the opening 40a of the detection unit 16, the pipette-side light shielding part 41 and the dark box-side light shielding part 42 are nested within each other.

While light generally travels linearly, due to the presence of the pipette-side light shielding part 41 and the dark box-side light shielding part 42 that are nested within each other, there is no linear optical path from the outside to the inside of the dark box 40. Therefore, the light cannot enter the dark box 40 from outside. Further, in order to prevent the external light from entering the dark box 40 by reflection between the pipette-side light shielding part 41 and the dark box-side light shielding part 42, the pipette-side light shielding part 41 and the dark box-side light shielding part 42 preferably have the front surfaces that absorb light. Specifically, the pipette-side light shielding part 41 and the dark box-side light shielding part 42 may be formed of, for example, a black material or may be painted in black.

While a cap or the like is used to shield light in the opening, it is required to narrow the gap of a contact part between the cap and the dark box in order to prevent the external light from entering through the gap. Therefore, when light is shielded using the cap, a highly accurate machine processing is required to form this shape.

On the other hand, the automatic analyzing apparatus 10 according to the first embodiment achieves the light shielding by the nested structure. Therefore, the light shielding is achieved without a contact between the dark box and the light shielding member. It is therefore possible to sufficiently shield light also in a space into which the pipette 12 is inserted from the opening part without requiring the highly accurate machine processing.

Further, the pipette-side light shielding part 41 and the dark box-side light shielding part 42 have a large degree of freedom regarding the vertical moving direction of the pipette 12. That is, when there is a part in which the pipette-side light shielding part of the pipette-side light shielding part 41 and the inside diameter part and the outside diameter part of the dark box-side light shielding part 42 overlap each other with respect to the horizontal surface direction, light can be shielded in any position.

It is therefore possible to perform the measurement in a plurality of positions in the height direction.

For example, the front surface of the reaction plate to be inserted into the pipette chip 20 may be divided into a plurality of sections in the direction of the axis that connects the opening part 21 and the nozzle part 23, antibodies different from one another may be immobilized on the respective sections to deal with a plurality of analytic items. Further, one section may be a section for measuring a blank.

When the measurement is performed by inserting the reaction plate having a plurality of sections into the pipette chip 20, the automatic analyzing apparatus 10 performs the measurement by keeping the pipette 12 at a predetermined height. After the measurement is performed, the automatic analyzing apparatus 10 changes the height of the pipette 12, stops the pipette 12, and performs the measurement. In the following processing, the measurement is performed the number of times corresponding to the number of sections at the height corresponding to each section. The processing of controlling the height of the pipette 12, dividing the signals that have been measured according to the height, and outputting the signals is achieved by a control device such as a CPU.

As described above, according to the automatic analyzing apparatus according to the first embodiment, the reaction plate including the plurality of sections is included in one pipette chip. When the measurement is performed in a plurality of positions corresponding to the reaction plate, noise caused by the stray light and the external light can be reduced and the highly-sensitive light measurement can be performed.

While the nested structure has the cylindrical shape in FIGS. 10 and 11, it may have a polygonal shape or the like.

On the other hand, when the nested structure has a cylindrical shape, the present invention can be applied also to a case in which the pipette and the pipette chip are rotated.

The present invention may be applied, for example, to a measurement of both surfaces. In this case, the both surfaces of the reaction plate may be modified differently, or only one surface may be modified and the other surface may be a blank. Further, the measurement unit and the measurement block unit may be rotated without rotating the pipette and the pipette chip. Furthermore, two measurement block units may be arranged so that they face each other to measure both surfaces of the reaction plate.

Furthermore, the analysis system including the pipette chip and the automatic analyzing apparatus according to the first embodiment is an all-in-one system in which all of the suction of the specimen or the reagent, the stirring, the cleaning, the reaction, and the detection due to the suction and the discharge are performed in the pipette chip 20.

A pump unit corresponding to this all-in-one system will be described.

Figure 12:
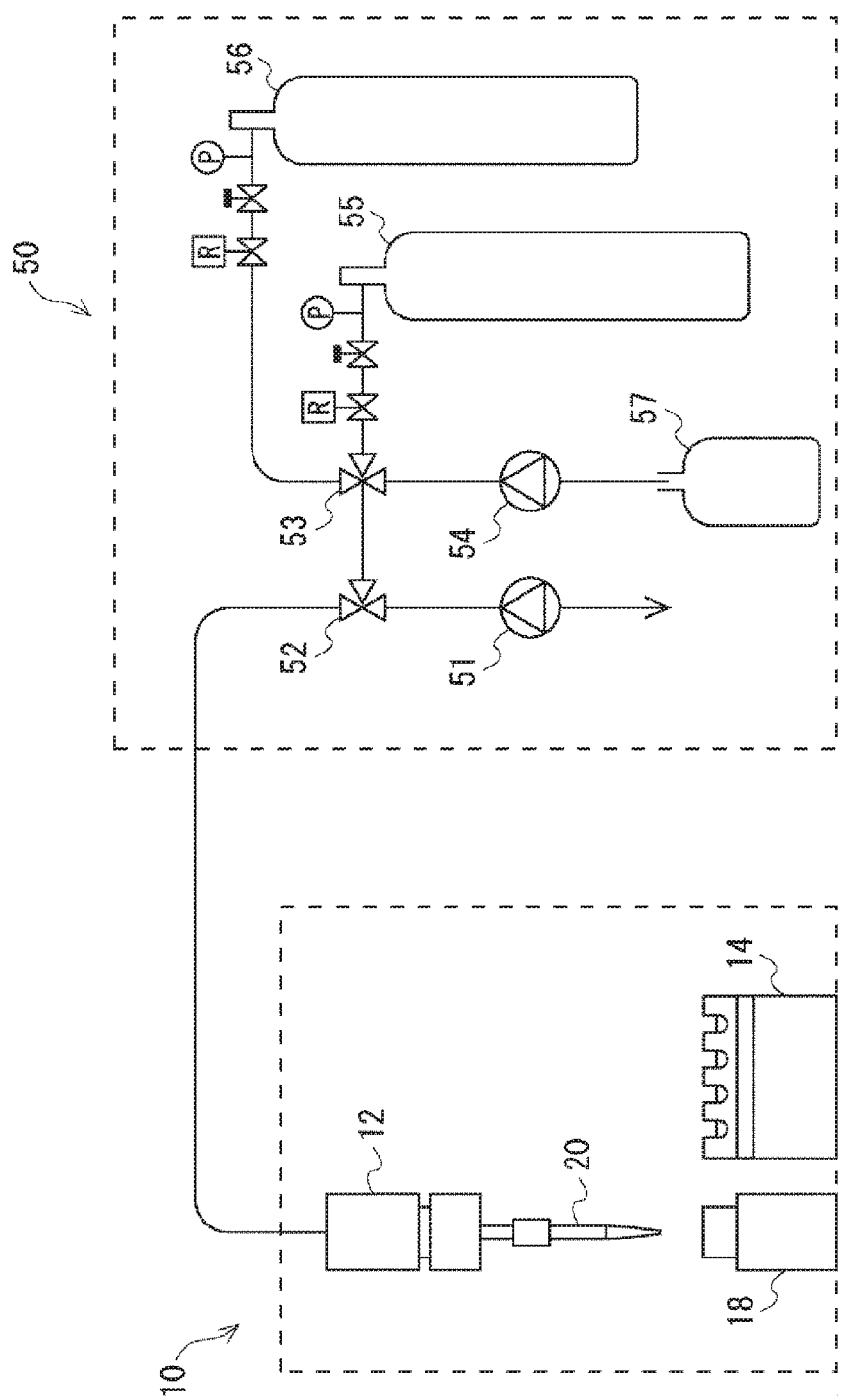
FIG. 12 is a diagram showing a schematic view of a pump unit of an analysis system according to the first embodiment.

FIG. 12 is a diagram showing a schematic view of the pump unit of the analysis system according to the first embodiment.

In FIG. 12, a pump unit 50 includes a suction pump 51 that sucks the specimen, three-way valves 52 and 53, a liquid sending pump 54, gas cylinders 55 and 56, and a washing liquid bottle 57.

The three-way valve 52 is a valve that is connected to the pipe from the pipette 12, switches the suction pump 51 and the three-way valve 53 connected to the delivery system, and connects one of the suction pump 51 and the three-way valve 53 to the pipette 12.

The three-way valve 53 is a valve that switches the liquid sending pump 54 that delivers solution, the gas cylinder 55 that delivers gas used for the stirring, and the gas cylinder 56 that delivers air, and is connected to one of the liquid sending pump 54, the gas cylinder 55, and the gas cylinder 56.

The liquid sending pump 54 is a pump that is connected to the washing liquid bottle 57 and delivers a washing liquid inside the bottle to the pipette 12.

The gas cylinder 56 is a cylinder filled with gas used for the stirring. An inert gas such as nitrogen or argon is suitably used as the gas used for the stirring. Alternatively, in place of the gas cylinder 56, a Pressure Swing Adsorption (PSA) device may be used to supply nitrogen gas.

The gas cylinder 56 is a cylinder filled with synthetic air in which the ratio of nitrogen to oxygen is the same as that in air. The gas cylinder 56 also delivers the synthetic air for stirring, similar to the gas cylinder 55. In place of the gas cylinder 56, a pump and a filter may be used to deliver atmosphere for stirring. In reality, the gas cylinders 55 and 56 deliver gas via a pressure-adjusting valve and a flow-adjusting valve at a pressure and a flow rate suitable for the delivery.

Next, an operation of the pump unit 50 will be described. The three-way value and the pump in each operation can be controlled using a control device such as a sequencer or a single-chip computer. In this case, an electric three-way valve is suitably used as the three-way valve.

First, when the specimen or the reagent is sucked into the pipette chip 20, the pump unit 50 switches the three-way valve 52 to connect the pipette 12 and the suction pump 51, operates the suction pump 51, and sucks the specimen or the reagent inside the reagent rack 14 inside the pipette chip.

Next, when the specimen and the reagent in the pipette chip 20 are stirred, the pump unit 50 connects the gas cylinder 55 or 56 to the pipette 12 via the three-way valves 52 and 53. Then the gas is flowed through the pipette chip 20 in a state in which it is arranged in a predetermined well.

After the reaction of the specimen and the reagent has advanced, the unreacted specimen is discarded. The pump unit 50 operates the liquid sending pump 54 and delivers the washing liquid inside the washing liquid bottle 57 to the pipette 12 via the three-way valves 52 and 53. The washing liquid pushes out the unreacted reagent in the pipette chip 20 to the waste bottle 18.

After that, when the pipette chip 20 is cleaned, the pump unit 50 further flows the washing liquid, cleans the measurement cell part 22 and the reaction plate 24 in the pipette chip 20, and flushes away the unreacted reagent. The unreacted reagent and the washing liquid that are flushed away is discarded to the waste bottle 18.

The suction, the stirring, the reaction, and the cleaning of these reagents are repeated to form a complex required for the measurement.

After that, the pipette chip 20 is conveyed into the aforementioned measurement unit 16 and the measurement is performed.

As described above, the analysis system according to the first embodiment includes the pump unit that communicates with the pipette and the mechanism that performs the suction and the delivery of liquid or gas, whereby all of the suction of the specimen or the reagent, the the stirring, the cleaning, the reaction, and the detection due to the suction and the discharge can be executed in the pipette chip. While the pump unit 50 is provided outside the automatic analyzing apparatus 10 in FIG. 11, the pump unit 50 may be provided in the automatic analyzing apparatus. A form in which the pump unit 50 is arranged in the lower part of the automatic analyzing apparatus and is integrated therein is suitably employed.

Second Embodiment

Next, an example of measuring a specific antigen in association with the prostate cancer using the automatic analyzing apparatus 10 will be described.

The respective wells of the reagent rack 14 contain a sample (serum), a block solution, an antibody reagent, and a fluorescent reagent. On the other hand, an antibody is immobilized on the front surface of the reaction plate 24 in the pipette chip 20. When the automatic analyzing apparatus 10 is used for a diagnosis of prostate cancer, an anti-free PSA specific monoclonal antibody is immobilized. The anti-free PSA specific monoclonal antibody is an anti-free PSA antibody that does not react with a complex PSA which is derived from clone 2E2. Specific antibodies include an 8A6 monoclonal antibody manufactured by Funakoshi Co., Ltd.

First, the pipette 12 is moved to a position directly above the chip rack 11 and is then moved downward, whereby the pipette chip 20 is mounted on the tip of the pipette 12.

Next, after the pipette 12 is elevated, it moves to a position directly above the reagent rack 14. The pipette 12 is then lowered to a height of the pipette chip 20 in the well of the reagent rack 14, and performs suction, reaction, discharge, and cleaning by a drive of the pump. The operations of the suction, the reaction, the discharge, and the cleaning are respectively executed in the sample (serum), the block solution, the antibody reagent, and the fluorescent reagent.

First, the pipette 12 sucks the blocking solution. Due to the blocking solution, the front surface of the reaction plate 24 is blocked.

Next, the pipette 12 discharges the blocking solution and sucks the sample. The measurement cell part 22 of the pipette chip 20 is filled with the sample. After that, by leaving it at 4° C. for five minutes to one hour, the antibody immobilized on the reaction plate 24 and the free PSA included in the sample are reacted.

Next, the pipette 12 discharges the sample and sucks the antibody reagent. When the automatic analyzing apparatus 10 is used for a diagnosis of prostate cancer, an anti-α2,3 linked sugar chain antibody, that is, a monoclonal antibody that specifically recognizes the sugar chain in which terminal sialic acid residues are linked to galactose through an α(2,3) linkage, is suitably used. Specific antibodies include an HYB4 monoclonal antibody manufactured by Wako Pure Chemical Industries, Ltd. By leaving it at 4° C. for five minutes to one hour, a complex of anti-free PSA antibody—free PSA—anti-α2,3 linked sugar chain antibody is formed on the reaction plate 24.

Next, the pipette 12 discharges the antibody reagent and sucks the fluorescent reagent. Specific fluorescent reagents include a fluorescent dye-labeled anti-mouse IgG3 antibody. By keeping it at room temperature for 5 to 45 minutes, a complex of anti-free PSA antibody—free PSA—anti-α2,3 linked sugar chain antibody-fluorescent reagent is formed on the reaction plate 24.

After the complex is formed, the pipette 12 moves the pipette chip 20 to the position of the detection unit 16 and lowers the pipette chip 20 at the position of the opening 40a.

The detection block unit 17 then detects the fluorescence emitted from the measurement cell part 22 of the pipette chip 20.

After the fluorescence is detected, the pipette 12 moves to a position directly above the waste bottle 18 by elevation and parallel translation, discharges the fluorescent reagent, and discards the fluorescent reagent into the waste bottle 18.

Last, the pipette 12 is moved to the chip disposal box 19, releases the pipette chip 20 by a releasing mechanism of the chip disposal box 19, and discards the pipette chip 20 into the chip disposal box 19.

According to the above operation, the automatic analyzing apparatus 10 is able to detect the prostate specific antigen.

Note that the present invention is not limited to the above embodiments and can be changed as appropriate without departing from the spirit of the present invention. For example, throughput can be improved by using a multiple-channel pipetter such as an 8-channel pipetter as the pipette.

REFERENCE SIGNS LIST

10 AUTOMATIC ANALYZING APPARATUS
11 CHIP RACK
12 PIPETTE
13 CONVEYANCE UNIT
14 REAGENT RACK
15 REACTION UNIT
16 DETECTION UNIT
17 DETECTION BLOCK UNIT
17a DARK BOX
20 PIPETTE CHIP
22 MEASUREMENT CELL PART
24 REACTION PLATE
31 UPPER STRUCTURE
32 LOWER STRUCTURE
34 TAPERED PART
40 DARK BOX
41 PIPETTE-SIDE LIGHT SHIELDING PART
42 DARK BOX-SIDE LIGHT SHIELDING PART
42b INSIDE DIAMETER PART
42c OUTSIDE DIAMETER PART

The invention claimed is:

1. An automatic analyzing apparatus comprising:
a pipette chip rack having at least one plane and capable of holding one or a plurality of pipette chips, each of the pipette chips including a measurement cell part through which light can be transmitted;
a pipette on which the pipette chip is mounted, the pipette sucking and discharging a specimen, wherein the pipette is surrounded by a first light shield comprising a light absorbing surface;
a conveyance unit for conveying the pipette on which the pipette chip has been mounted;
a measurement unit including an opening that receives the pipette chip therein and measuring light emitted from the specimen inside the pipette chip; and
a detection unit comprising a second light shield shielding an opening of the detection unit, wherein the second light shield has an opening for receiving a tip of the pipette, wherein the first light shield and the second light shield having a nested structure when the pipette is received at the detection unit,
wherein:
the pipette chip rack includes a guide that orients one plane of the pipette chip to a specific direction on a horizontal surface, the conveyance unit conveys, after the pipette chip arranged in the pipette chip rack is mounted on the pipette, the pipette chip into the measurement unit and arranges the pipette chip so that the plane of the pipette chip becomes orthogonal to an optical axis of the measurement unit, and the measurement unit measures light emitted from the specimen in the pipette chip or light that has transmitted the specimen.

2. The automatic analyzing apparatus according to claim 1, wherein the second light shield has a nested structure which includes a first cylinder for receiving the pipette, wherein an end of the first cylinder in contact with the detection unit is closed and one or a plurality of second cylinders having diameters different from a diameter of the first cylinder surrounds the first cylinder in increasing concentric circles.

3. The automatic analyzing apparatus according to claim 1, wherein:

the pipette chip rack includes the guide that orients one plane of the pipette chip in a direction vertical to the optical axis of the measurement unit, and the conveyance unit mounts the pipette chip arranged in the pipette chip rack onto the pipette and then conveys the pipette chip into the measurement unit by parallel translation.

4. The automatic analyzing apparatus according to claim 1, wherein the pipette chip rack is tapered above an upper part of the guide.

5. The automatic analyzing apparatus according to claim 1, comprising a controller for controlling the conveyance unit and the detection unit, wherein:

the controller moves the pipette in a vertical direction in a position of the opening and outputs an instruction to stop the pipette at a plurality of heights to the conveyance unit, and the controller divides an intensity of a signal received by the detection unit for each height at which the pipette is stopped and outputs the signal.

6. The automatic analyzing apparatus according to claim 1, comprising a pump unit that sends gas to the pipette, wherein the pipette includes a hollow part that communicates the pump unit with the pipette chip and supplies the gas to the pipette chip.

7. An analysis system comprising the automatic analyzing apparatus according to claim 1 wherein the pipette chip has at least one plane and further comprises a measurement cell part through which light can be transmitted, wherein:

the conveyance unit mounts the pipette chip arranged in the pipette chip rack onto the pipette, conveys the pipette chip into the measurement unit, and arranges the pipette chip so that the plane of the pipette chip becomes orthogonal to the optical axis of the measurement unit, and the measurement unit measures light emitted by the specimen in the pipette chip.

8. The analysis system according to claim 7, wherein:

the automatic analyzing apparatus comprises a reagent rack including one or a plurality of wells, each containing a reagent, the pipette chip includes a reaction plate in the chip, and the pipette sucks the reagent included in the well into the pipette chip and causes the reaction plate and the reagent to be reacted.

9. The analysis system according to claim 7, wherein:

the automatic analyzing apparatus comprises a reagent rack including one or a plurality of wells, each containing a reagent, the pipette chip includes a reaction plate in the chip, the reaction plate having a front surface including the reagent, and the pipette sucks the reagent included in the well into the pipette chip and causes the reagent included in the reaction plate and the reagent that has been sucked to be reacted.

10. The analysis system according to claim 8, wherein:

the reagent rack holds, in each well, an antibody and a fluorescent label that specifically react against a prostate specific antigen in which a terminal sialic group is linked to galactose at a position of α2,3, and the reaction plate immobilizes an antibody that specifically reacts against a free prostate specific antigen.

11. The analysis system according to claim 8, wherein the reaction plate includes a plurality of sections comprising reagent immobilizing components.

12. The analysis system according to claim 11, wherein one of the sections does not comprise a reagent immobilizing components.

13. An operation method of the automatic analyzing apparatus according to claim 1, the operation method comprising processes of:

moving, by the conveyance unit, the pipette to a position directly above the pipette chip placed on the pipette chip rack;

moving vertically, by the conveyance unit, the pipette to mount the pipette chip onto the pipette;

sucking, by the pipette, the specimen into the pipette chip;

conveying, by the conveyance unit, the pipette chip into the detection unit to arrange the pipette chip so that the plane of the pipette chip becomes orthogonal to the optical axis of the measurement unit; and measuring, by the detection unit, light emitted from the specimen in the pipette chip.

* * * * *